United States Patent [19]

Lifshey

[11] Patent Number: 5,464,122

[45] Date of Patent: Nov. 7, 1995

[54] NON-STREAMING OPHTHALMIC TIP AND DELIVERY DEVICE

[75] Inventor: Arthur L. Lifshey, East Brunswick, N.J.

[73] Assignee: Merck & Co., Inc., Rahway, N.J.

[21] Appl. No.: 265,351

[22] Filed: Jun. 24, 1994

[51] Int. Cl.⁶ ............................. B65D 47/18; B67B 7/24
[52] U.S. Cl. ........................... 222/83; 222/420; 401/132; 401/262
[58] Field of Search ..................... 401/262, 132; 222/420, 421, 422, 541, 83, 83.5

[56] References Cited

U.S. PATENT DOCUMENTS

| 2,411,435 | 11/1946 | Kirselenbaum | 222/421 |
| 2,671,577 | 3/1954 | Remington et al. | 222/541 X |
| 3,454,196 | 7/1969 | Hazard | 222/541 X |
| 5,052,589 | 10/1991 | O'Mera | 222/541 X |

FOREIGN PATENT DOCUMENTS

| 228751 | 7/1987 | European Pat. Off. | 222/420 |
| 2906818 | 11/1979 | Germany | 222/420 |
| 372497 | 6/1939 | Italy | 222/421 |

*Primary Examiner*—Steven A. Bratlie
*Attorney, Agent, or Firm*—Frank P. Bigley; Mark R. Daniel; Joseph F. DiPrima

[57] ABSTRACT

This invention consists of an ophthalmic dispensing tip formed by injection molding, which has a one-piece molded tip to be used with a mating cap, the tip having an internally molded breakaway barrier membrane inside the flow channel, and the cap having a shaped stud fitting inside the tip, so that the final clockwise half-turn of the cap pushes the stud against the barrier and displaces it, thereby creating a restricted path through which the contents are dispensed.

1 Claim, 7 Drawing Sheets

NON-STREAMING OPHTHALMIC TIP AND DELIVERY DEVICE

TECHNICAL FIELD

This invention relates to a liquid dispensing tip and cap especially useful in the dispensing of ophthalmic drugs which typically need to be dispensed in the form of a drop, and a novel method of manufacturing it.

BACKGROUND OF THE INVENTION

The present invention pertains to the art of liquid dispensers, and, more particularly, to a dispensing tip for accurately dispensing small droplets of liquid. The invention is particularly applicable for use as an eyedropper to dispense ophthalmic drugs and will be described with particular reference thereto although it will be appreciated that the invention has other and broader applications.

Medicant drop dispensers of the type to which the present invention pertains are available in various sizes and shapes for the numerous medicines and solutions which are available for the care and comfort of the human eye. Such dispensers are basically comprised of a relatively small compressible plastic container or vial provided with a dispensing tip and cap.

One problem associated with conventional eyedroppers is the difficulty in accurately controlling the amount of medicine dispensed, i.e., the number of drops dispensed. Many conventional eyedroppers utilize one or a combination of methods to achieve single drop control.

One method uses a highly compliant plastic bottle which the user squeezes to dispense a drop. The extensive deflection of the bottle creates an significant internal air pressure within the vial which expels the liquid through the tip. In order to prevent a continuous stream of liquid medicant from being expelled, and to create single drops, these bottles sometimes incorporate a flow restriction at the inlet of the tip or nozzle. This flow restriction tends to limit the number of drops expelled during a single squeeze. It limits the liquid medicant flow rate favoring the formation of individual drops releasing from the dropper tip rather than a continuous stream. Unfortunately, the creation of a very small molded orifice, frequently as small as 0.005" (0.13 mm) in diameter creates manufacturing difficulties, since the plastic injection molds must have corresponding small fragile (0.005" dia./ 0.13 mm dia.) core pins.

SUMMARY OF THE INVENTION

The present invention contemplates a new and improved tip and cap for ophthalmic use, which overcomes the above-referred to manufacturing difficulties and which accurately dispenses droplets of liquid medicant at desired locations as discrete drops. Single drops having a volume of approximately 30–50 microliters are typical in the art, but larger or smaller drops, can be provided by adjusting size and geometry of the tip.

In accordance with the present invention there is provided an improved tip, or drop dispenser for use with a closed compressible container. The preferred tip is integrated into a simple one piece molded device, together with a mated cap in combination which is best understood by reference to the accompanying drawings. The tip/cap combination also serves as a means for providing an hermetically sealed tip which can be activated (opened) only when ready for use. This can be accomplished by only partially assembling the cap onto the tip, so s that the cap (2) does not displace the membrane in the tip. The tip thus remains hermetically sealed, eliminating the possibility of minor leaks of liquid or vapor during long storage periods.

Figure 1:
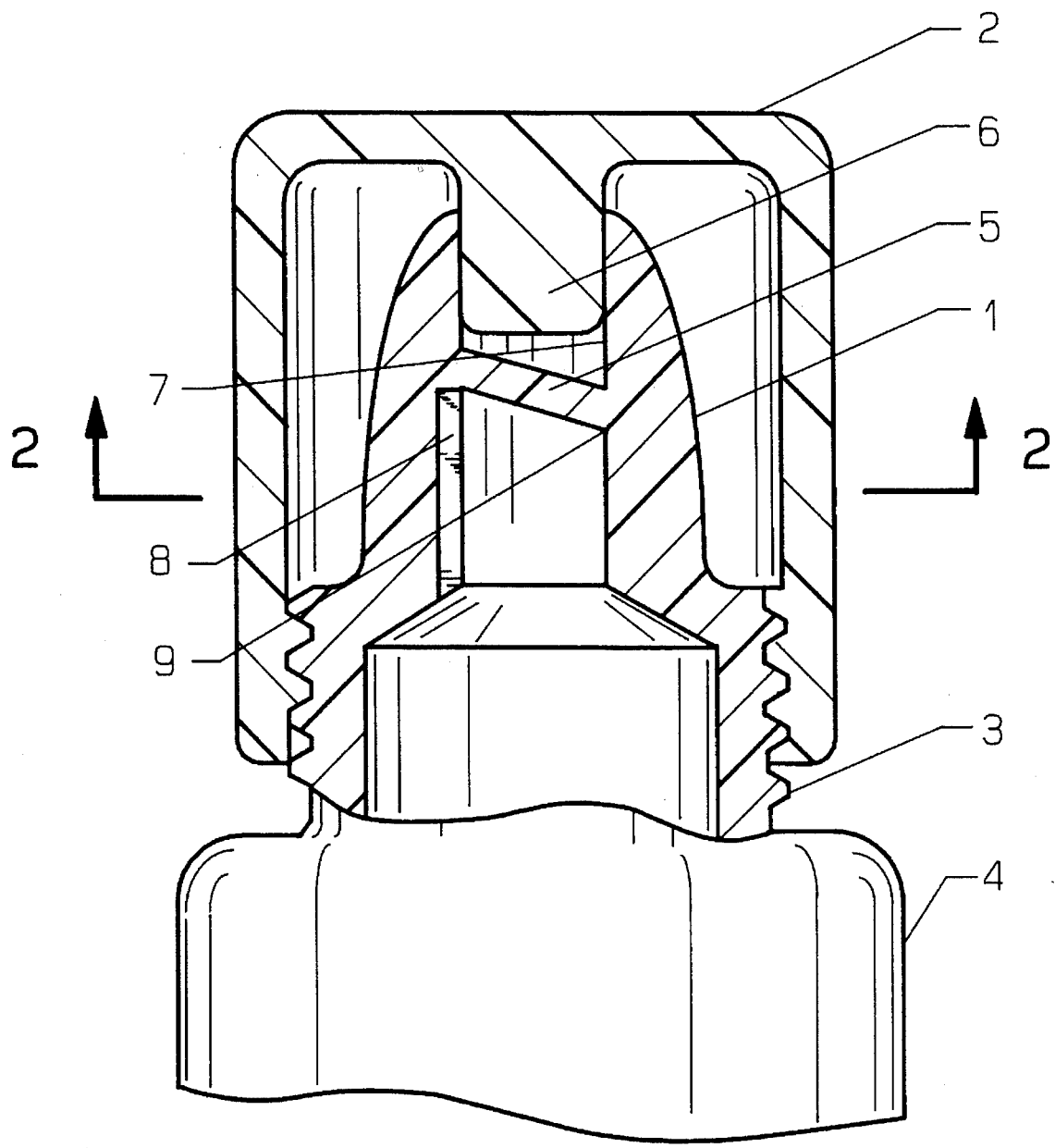
FIG. 1 is a vertical sectional view of the one-piece molded tip having a cap with screw threads engaged around the tip.

The actual bottle design is not a critical part of this invention. Any of the ophthalmic containers presently available can be used with the tip of this invention. The bottle design illustrated, which is especially preferred, is one having a limited displacement area, such as described in the invention claimed in U.S. Ser. No. 08/200,076, filed Dec. 22, 1993.

Referring to the drawings, the key aspects of this invention are described as follows.

In FIG. 1, the ophthalmic tip, shown generally at 1, is protected by a cap 2, attached through screw threads 3. The bottle, which can be any type bottle useful for dispensing ophthalmic medicaments, is indicated generally at 4.

The cap 2 serves as a "seal-break". The tip is formed with a dislodgeable barrier 5 across the opening. The embodiment shown is eliptically shaped, and slanted so that it is attached higher inside the tip, at a point above a side slot 8. Other embodiments can include a circular or spherical barrier attached at circumferentially to the inside wall of the tip 1. The inside of the cap 2 fitting over the nozzle opening is fitted with a suitably sized and shaped integrally molded stud 6. The cap 2 can be designed so that a final clockwise half-turn of the cap pushes the stud 6 against the barrier 5 and downwardly displaces it while it remains attached at hinge point 9 to inside wall 7. Alternatively, the cap and bottle may be so designed that the stud 6 is moved downward against barrier 5 by axial force applied to the cap. Another embodiment of this invention would have stud 6 completely dislodge barrier 5 with a new position, which would break the hermetic seal and create a suitable flow restriction. In all cases, the barrier would be captivated in its new open position by friction fit, undercuts, or other mechanical means, allowing it to function as a flow restrictor able to resist the internal pressure generated in the vial during dispensing. Alternatively, the slot 8 in FIG. 2 may be of various sizes to allow for flow characteristics and viscosity of diverse fluids. Slot 8 may also consist of any number of shallow slots, as dictated by the flow properties.

The restricted flow channel side slot 8 or slots is an important part of this invention, as it serves to aid in the prevention of a stream of medicament.

Figure 2:
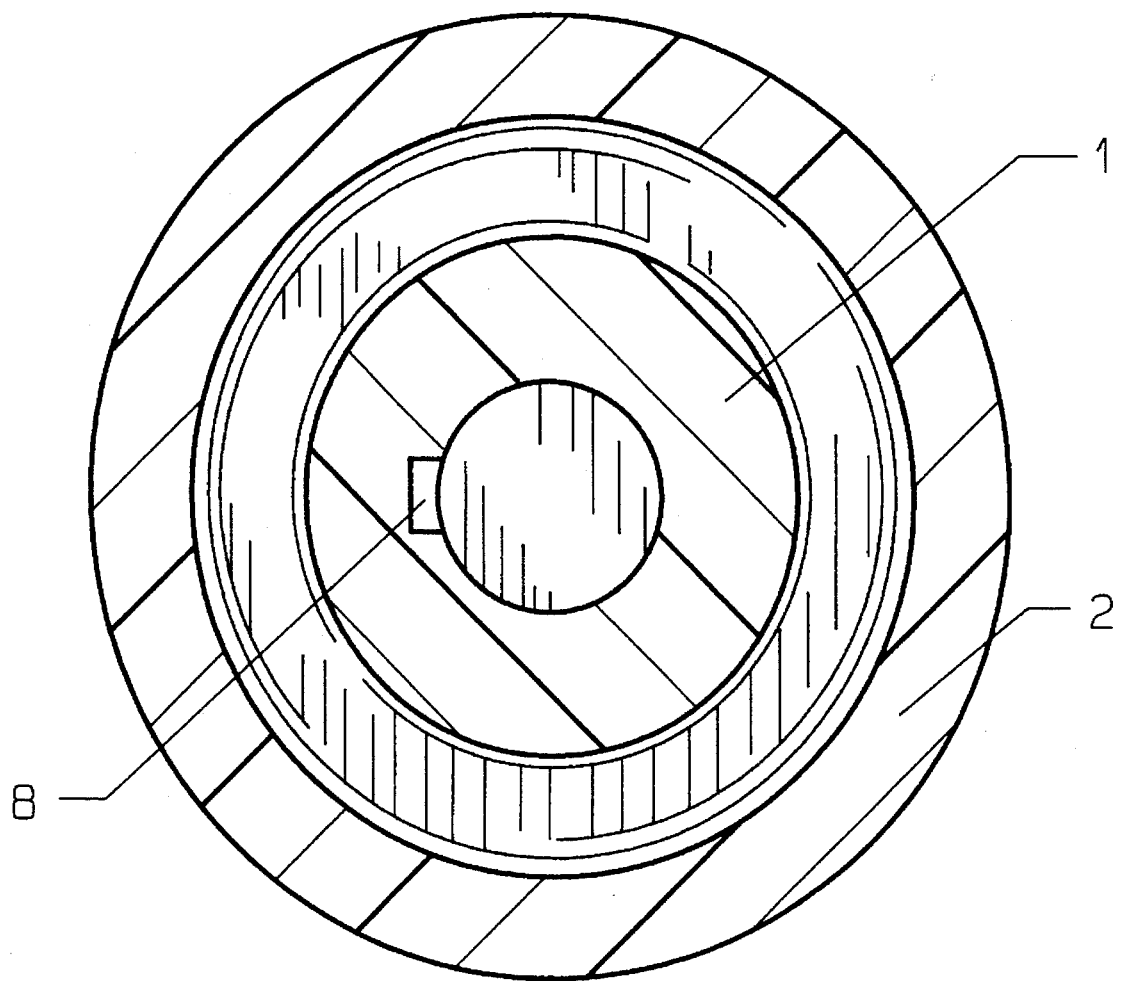
FIG. 2 is a cross-section of FIG. 1 taken along line 2—2, showing a restricted flow channel side slot.
Figure 2A:
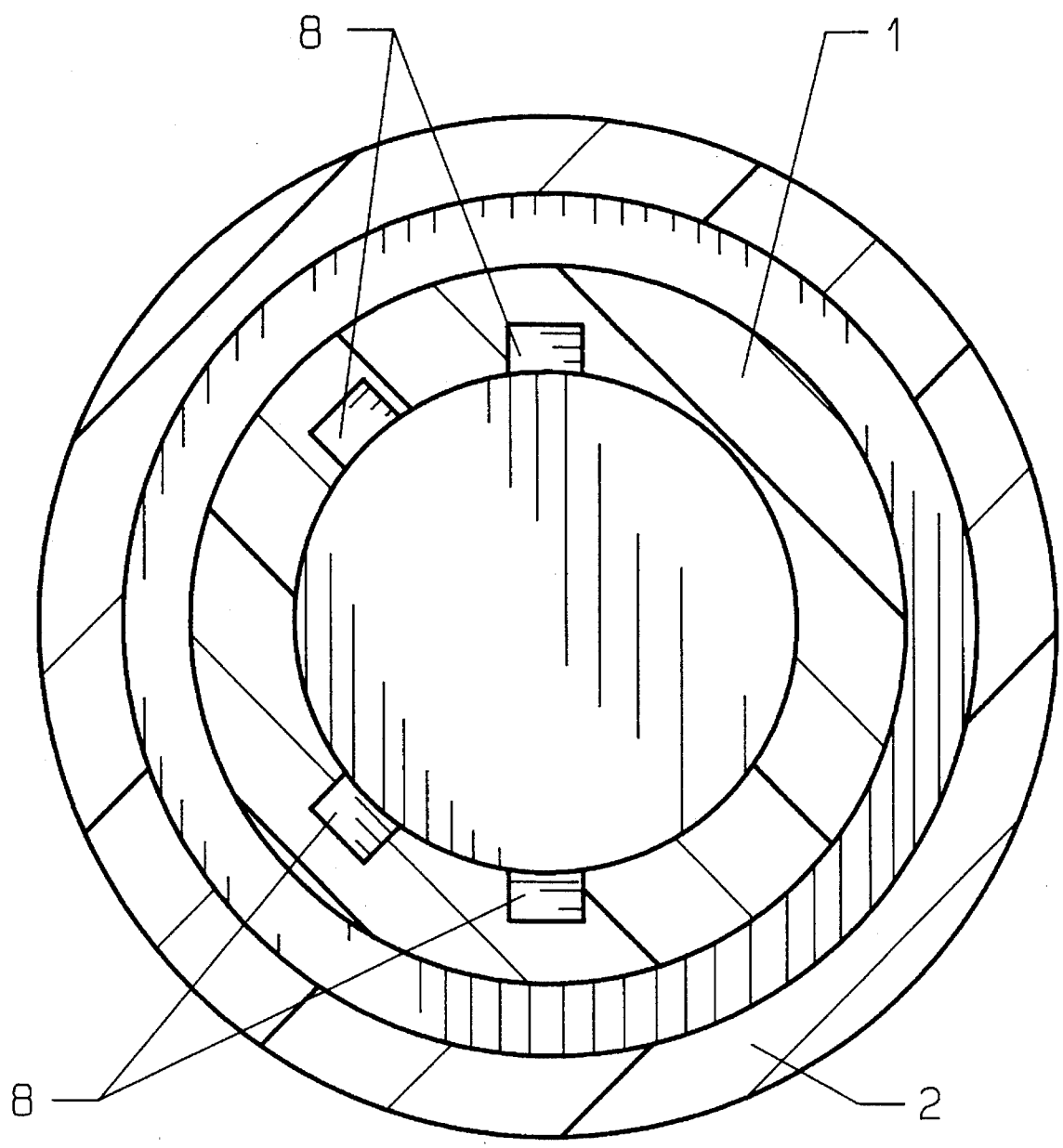
FIGS. 2a and 2b are alternate embodiments showing other restricted slot(s) or groove(s).
Figure 2B:
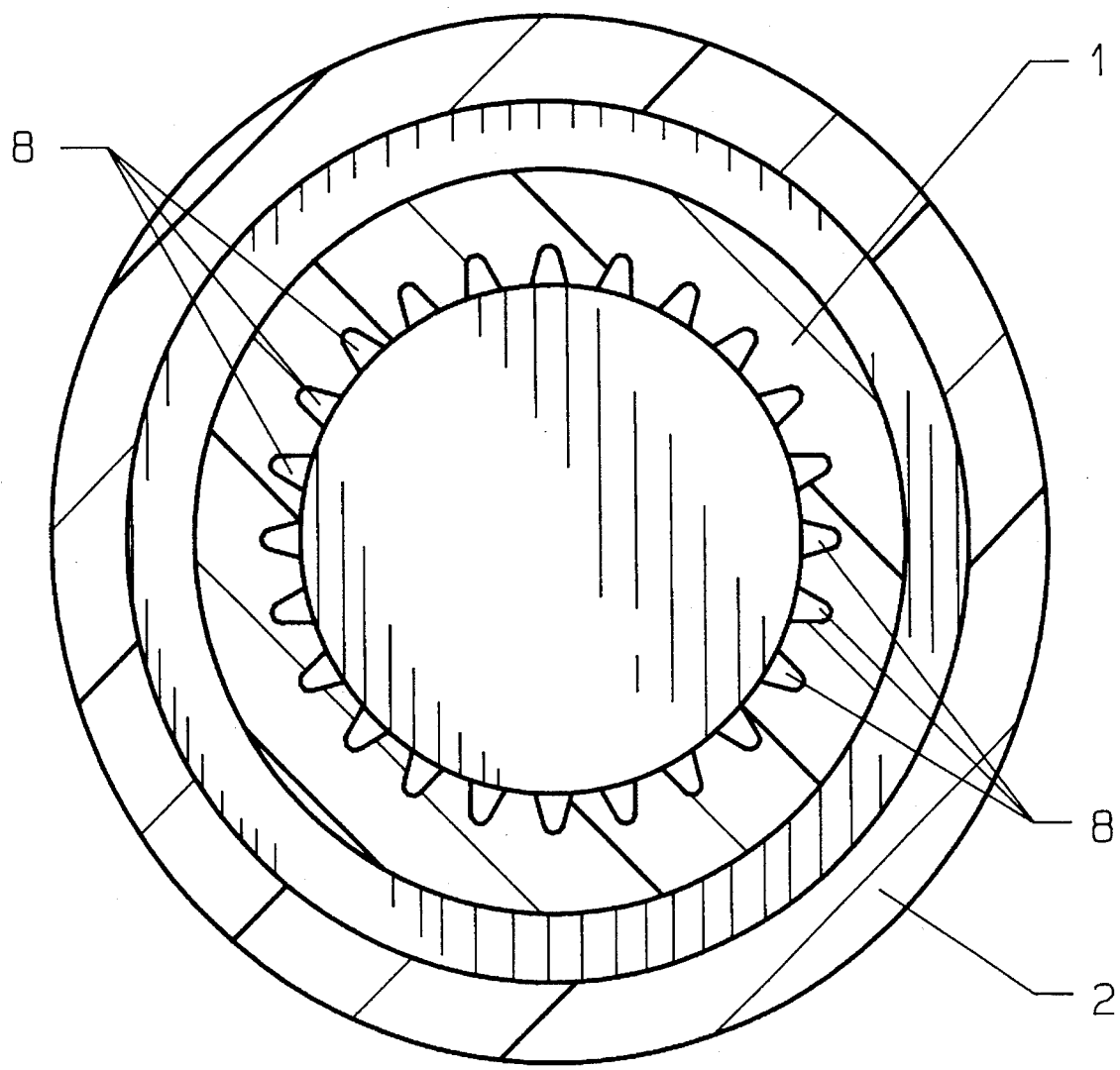
Figure 3:
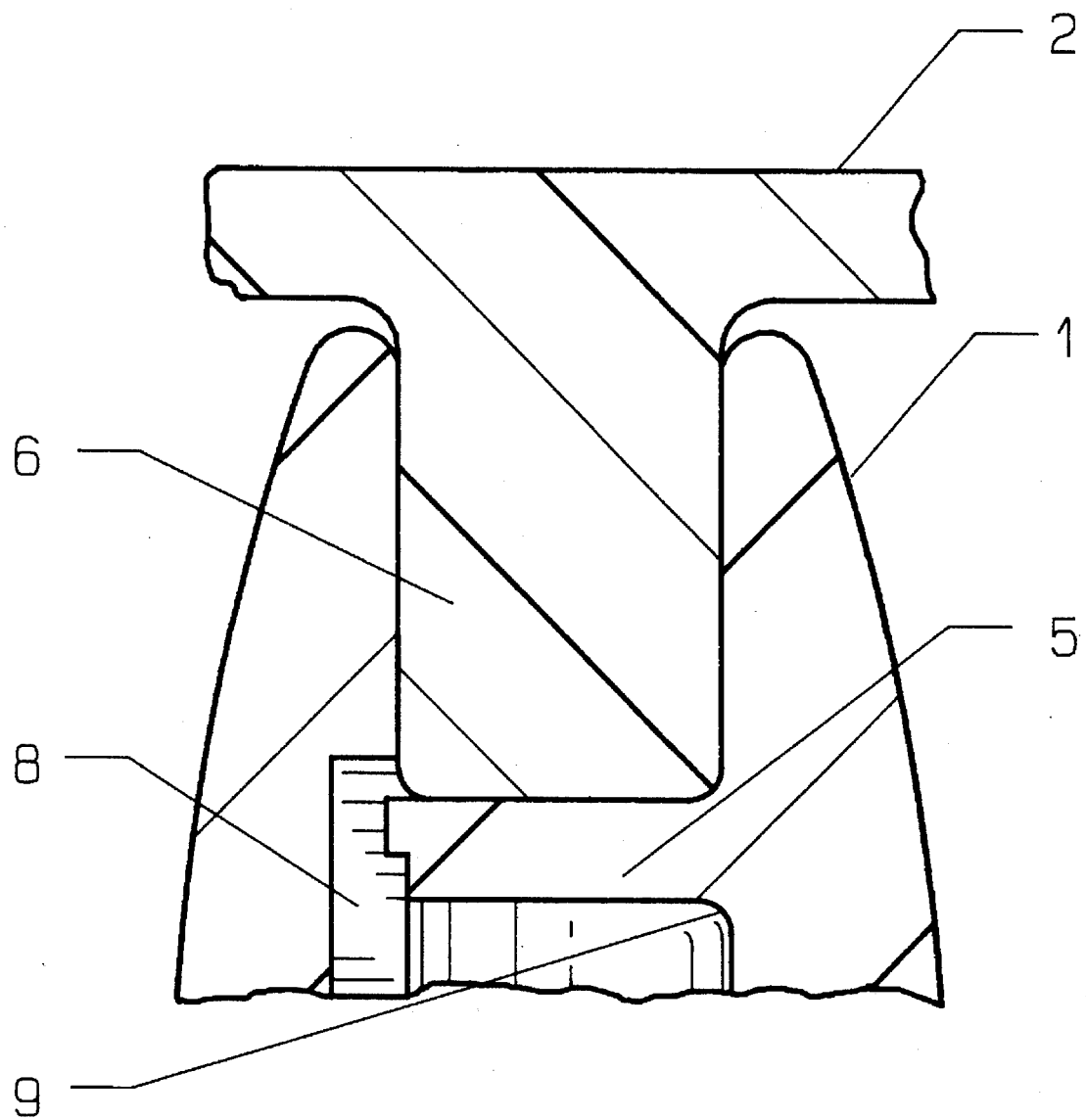
FIGS. 3 and 4 are vertical sectional views of the tip showing the action in opening the cap and the restricted flow path, which prevents streaming.

Its shape in cross section is shown in FIGS. 2, and alterative embodiments 2A and 2B wherein it can clearly be seen as molded slot(s) or groove(s) in the nozzle channel.

Figure 4:
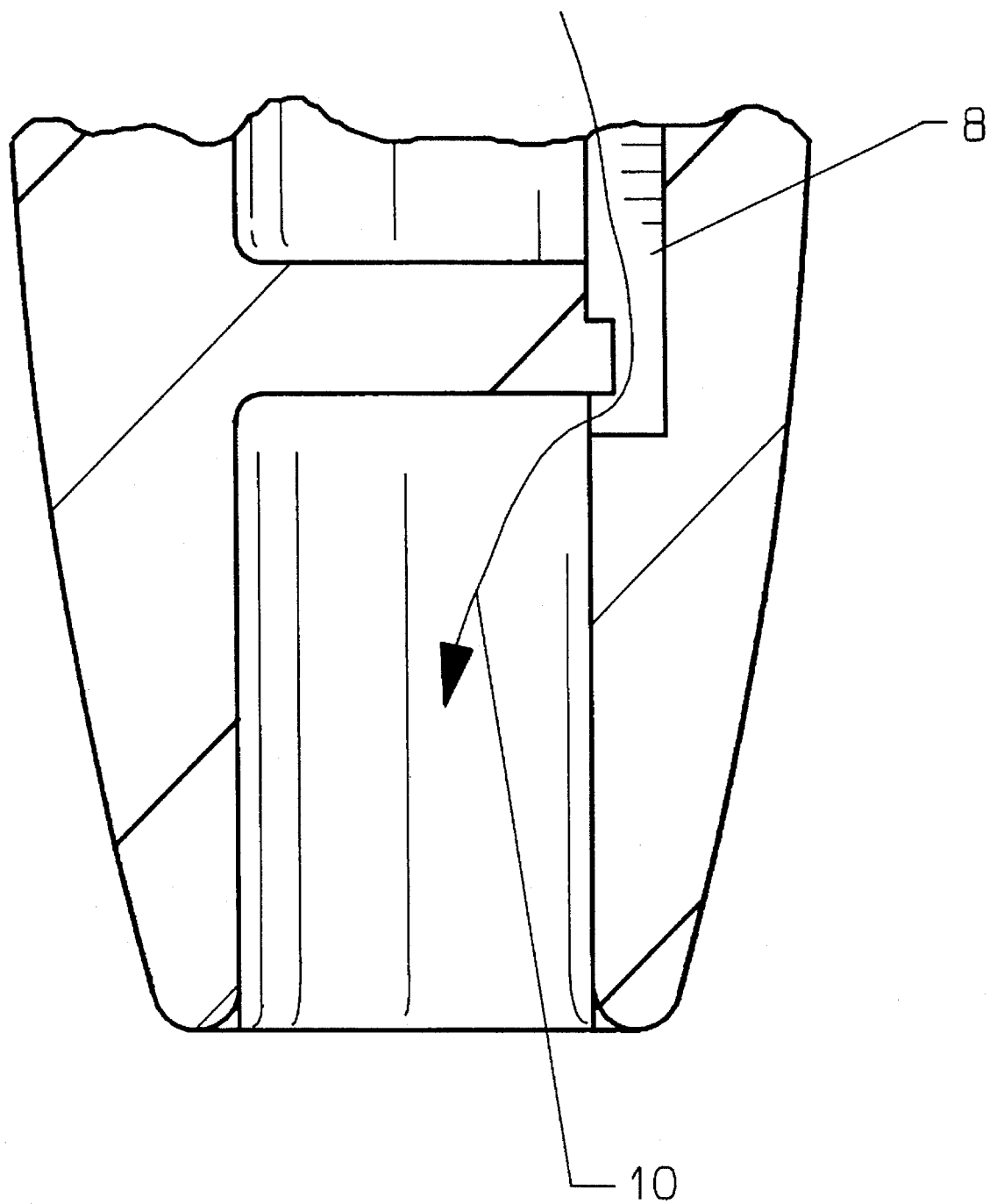

Once the cap 2 is pushed or screwed down onto the tip 1, and the barrier 5 is displaced downwardly, the liquid contents can exit through the side slot 8 by flowing around the barrier 5, as shown in FIG. 4, which is an upside-down vertical section. The arrow 10 in FIG. 4 demonstrates the fluid path flow. The stud 6 of cap 2 is designed so that the stud 6 serves as a leak-proof closure for the bottle upon recapping after activation.

The restricted flow channel side slot 8 is formed during the injection molding process by using a small radially outward projection on a relatively large sturdy core pin.

The ophthalmic dispensing tip and cap of this invention can be injection molded of a suitable plastic, such as polyethylene or polypropylene.

Figure 5:
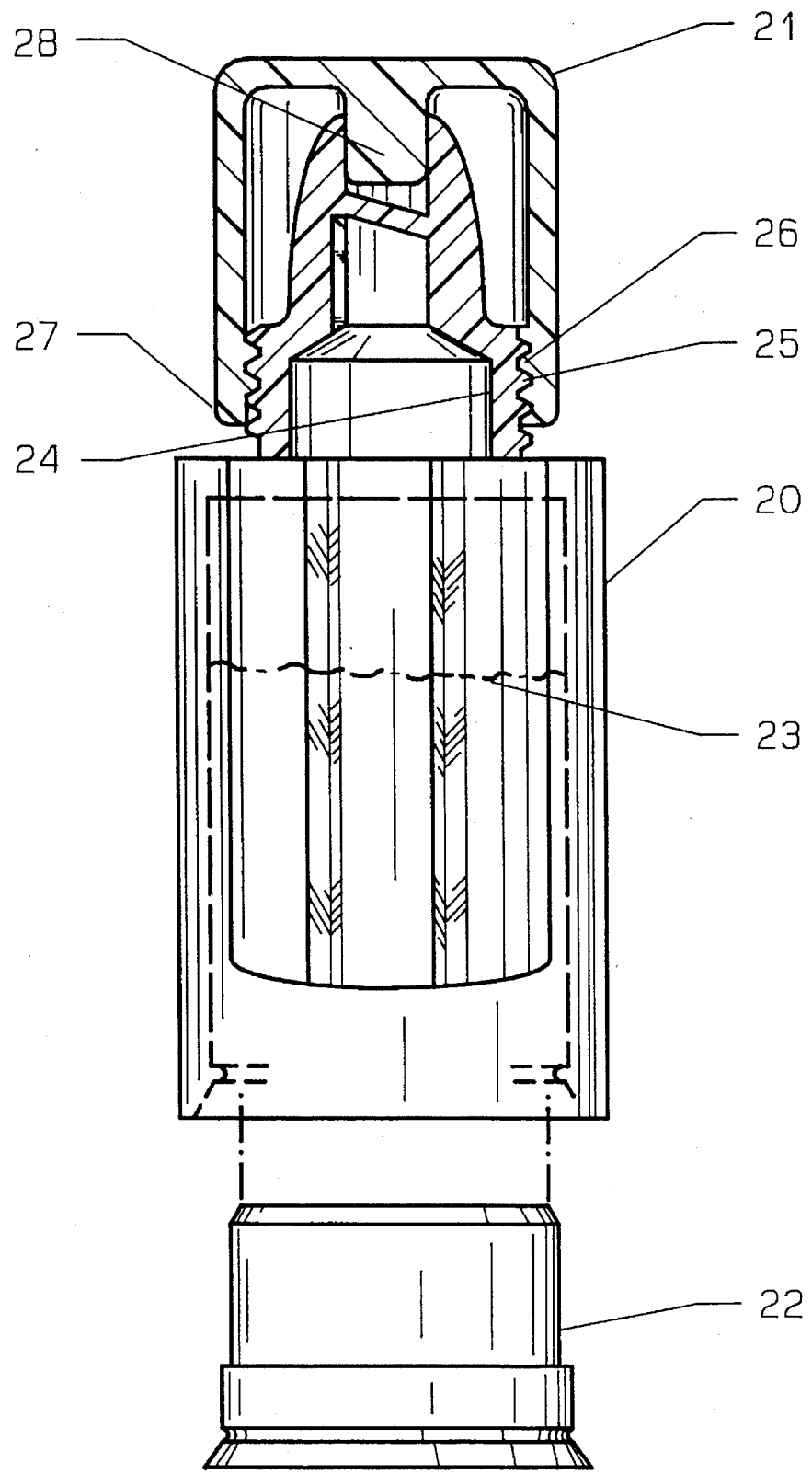
FIG. 5 is a diagrammatic view of an example of an ophthalmic container having the tip with cap of this invention in place.

In one preferred embodiment, the tip of this invention is molded as part of a bottle having a limited displacement side member as illustrated in FIG. 5. The combination of a limited displacement bottle and the flow restriction in the instant dispensing tip are a way to prevent streaming. FIG. 5 is a diagrammatic view of this embodiment of the ophthalmic container including the tip and cap of the instant invention. As noted, the invention of the bottle of FIG. 5 is an independent invention, previously filed on Dec. 22, 1993, U.S. Ser. No. 08/200,676.

FIG. 5 shows the tip and cap of the present invention in place on the bottle of the independent invention, comprised of a compressible plastic container or vial 20, a cap member 21, and a bottom closure 22. Container or vial 20 contains a supply of liquid 23, medicament for instance, to be dispensed in droplet form. The container 20 has an integral reduced diameter open neck portion 24 provided with external helical screw threads 25 over the uppermost part of the neck end portion as shown in FIG. 5. The screw threads 25 are adapted to matingly engage internal threads 26 on cap member 21 to thereby attach the latter in place on container 20 in liquid-tight relation thereto.

Cap member 21 comprises a generally cylindrical mounting or base portion 27 and a inside nozzle end portion stud 28 projecting endwise therefrom.

What is claimed is:

1. An ophthalmic tip and cap system providing non-streaming drop control, the tip having an internally molded dislodgeable barrier attached inside the channel of the tip at a slant, the higher point of attachment being above a side slot in said channel; and the lower point of attachment being opposite said slot; the cap having a stud shaped to fit inside said channel, so that the downward axial movement of the cap displaces the barrier downward from the higher point of attachment in said channel, said barrier remaining attached inside said channel at the lower point of attachment.

\* \* \* \* \*